United States Patent
Okumu (10) Patent No.: US 6,992,065 B2
(45) Date of Patent: Jan. 31, 2006

(54) SUSTAINED RELEASE FORMULATIONS

(75) Inventor: Franklin Okumu, Oakland, CA (US)

(73) Assignees: Genentech, Inc., South San Francisco, CA (US); Durect Corporation, Cupertino, CA (US)

( * ) Notice: Subject to any disclaimer, the term of this patent is extended or adjusted under 35 U.S.C. 154(b) by 0 days.

(21) Appl. No.: 09/839,684

(22) Filed: Apr. 19, 2001

(65) Prior Publication Data

US 2002/0001631 A1  Jan. 3, 2002

Related U.S. Application Data (60) Provisional application No. 60/198,209, filed on Apr. 19, 2000.

(51) Int. Cl.
- A61K 38/27 (2006.01)
- A61K 47/08 (2006.01)
- A61K 47/14 (2006.01)
- A61K 47/26 (2006.01)

(52) U.S. Cl. .................... 514/21; 424/423; 514/6; 514/772; 514/777; 514/785; 514/788; 530/399

(58) Field of Classification Search ........... 424/422, 424/423, 424, 425, 426, 484, 488, 489, 490, 424/491, 493, 498, 499, 502; 514/6, 12, 514/21, 772, 777, 785, 786, 787, 788; 530/399, 530/400

See application file for complete search history.

(56) References Cited

U.S. PATENT DOCUMENTS

| | | | |
|---|---|---|---|
| 4,016,273 A * | 4/1977 | Sieger et al. | 514/211.13 |
| 4,297,344 A | 10/1981 | Schwinn et al. | 530/381 |
| 4,938,763 A | 7/1990 | Dunn et al. | 604/891.1 |
| 4,975,271 A | 12/1990 | Dunn et al. | 514/708 |
| 5,077,049 A | 12/1991 | Dunn et al. | 424/426 |
| 5,096,885 A | 3/1992 | Pearlman et al. | 514/12 |
| 5,133,981 A | 7/1992 | Harkrader et al. | 424/195.1 |
| 5,242,910 A | 9/1993 | Damanj | 514/152 |
| 5,278,201 A | 1/1994 | Dunn et al. | 523/113 |
| 5,278,202 A | 1/1994 | Dunn et al. | 523/113 |
| 5,324,519 A | 6/1994 | Dunn et al. | 424/426 |
| 5,324,520 A | 6/1994 | Dunn et al. | 424/435 |
| 5,340,849 A | 8/1994 | Dunn et al. | 523/113 |
| 5,368,859 A | 11/1994 | Dunn et al. | 424/426 |
| 5,411,951 A * | 5/1995 | Mitchell | 514/12 |
| 5,487,897 A | 1/1996 | Polson et al. | 424/426 |
| 5,556,905 A | 9/1996 | Frappier et al. | 524/311 |
| 5,589,167 A | 12/1996 | Cleland et al. | 424/85.7 |
| 5,591,713 A | 1/1997 | Igari et al. | 514/8 |
| 5,599,552 A | 2/1997 | Dunn et al. | 424/423 |
| 5,651,986 A | 7/1997 | Brem et al. | 424/484 |
| 5,665,394 A | 9/1997 | Igari et al. | 424/501 |

(Continued)

FOREIGN PATENT DOCUMENTS

EP  0 216 485  4/1987

(Continued)

OTHER PUBLICATIONS

U. S. Provisional Application 60/214,168, filed Jun. 26, 2000.*

(Continued)

*Primary Examiner*—Jeffrey Edwin Russel
(74) *Attorney, Agent, or Firm*—Evan Law Group LLC (57) ABSTRACT

A composition for sustained release comprises a carrier material containing a non-polymeric, non-water soluble liquid material having a viscosity of at least 5,000 cP at 37° C. that does not crytallize neat under ambient physiological conditions, a multivalent metal cation, and growth hormone.

49 Claims, 11 Drawing Sheets

U.S. PATENT DOCUMENTS

| | | | |
|---|---|---|---|
| 5,747,058 A | 5/1998 | Tipton et al. | 424/423 |
| 5,780,044 A | 7/1998 | Yewey et al. | 424/426 |
| 5,783,205 A | 7/1998 | Berggren et al. | 424/426 |
| 5,851,229 A | 12/1998 | Lentz et al. | 623/1 |
| 5,889,035 A * | 3/1999 | Strupczewski et al. | 514/373 |
| 5,912,015 A | 6/1999 | Bernstein et al. | 424/484 |
| 5,945,115 A | 8/1999 | Dunn et al. | 424/422 |
| 5,968,542 A | 10/1999 | Tipton | 424/423 |
| 5,972,370 A | 10/1999 | Eckenhoff et al. | 424/424 |
| 5,981,489 A | 11/1999 | Stevenson et al. | 514/15 |
| 6,039,977 A | 3/2000 | Venkatraman et al. | 424/486 |
| 6,051,259 A | 4/2000 | Johnson et al. | 424/502 |
| 6,051,558 A | 4/2000 | Burns et al. | 514/15 |
| 6,066,619 A | 5/2000 | Stevenson et al. | 514/12 |
| 6,080,429 A | 6/2000 | Cleland et al. | 424/489 |
| 6,087,324 A | 7/2000 | Igari et al. | 514/2 |
| 6,110,503 A | 8/2000 | Rickey et al. | 424/501 |
| 6,113,943 A | 9/2000 | Okada et al. | 424/457 |
| 6,113,947 A | 9/2000 | Cleland et al. | 424/489 |
| 6,120,789 A | 9/2000 | Dunn | 424/426 |
| 6,124,261 A | 9/2000 | Stevenson et al. | 514/12 |
| 6,130,200 A | 10/2000 | Brodbeck et al. | 514/2 |
| 6,143,314 A | 11/2000 | Chandrashekar et al. | 424/426 |
| 6,146,662 A | 11/2000 | Jao et al. | 424/473 |
| 6,165,508 A | 12/2000 | Tracy et al. | 424/487 |
| 6,174,547 B1 | 1/2001 | Dong et al. | 424/463 |
| 6,190,700 B1 | 2/2001 | Okada et al. | 424/499 |
| 6,191,107 B1 | 2/2001 | Yamagata et al. | 514/12 |
| 6,197,350 B1 | 3/2001 | Yamagata et al. | 424/501 |
| 6,245,806 B1 | 6/2001 | Dombrowski et al. | 514/450 |
| 6,267,958 B1 | 7/2001 | Andya et al. | 424/130.1 |
| 6,328,979 B1 * | 12/2001 | Yamashita et al. | 424/400 |
| 6,413,536 B1 | 7/2002 | Gibson et al. | 424/423 |
| 6,429,296 B2 | 8/2002 | Yamagata et al. | 530/399 |
| 6,719,992 B2 * | 4/2004 | Jeng et al. | 424/422 |

FOREIGN PATENT DOCUMENTS

| | | |
|---|---|---|
| EP | 0 484 387 B1 | 1/1994 |
| MX | 173182 A | 7/1994 |
| WO | WO 89/03671 | 5/1989 |
| WO | WO 92/17200 | 10/1992 |
| WO | WO 92-17200 | 10/1992 |
| WO | WO 94/12158 | 6/1994 |
| WO | WO 98/27962 A2 | 7/1998 |
| WO | WO 98/27963 A2 | 7/1998 |
| WO | WO 99/33491 A1 * | 7/1999 |
| WO | WO 00/38652 | 7/2000 |
| WO | WO 00/78335 | 12/2000 |
| WO | WO 01/28524 | 4/2001 |

OTHER PUBLICATIONS

Gray et al., "Cloning of Human Tumor Necrosis Factor (TNF) Receptor cDNA and Expression of Recombinant Soluble TNF-Binding Protein ", *Proc. Natl. Acad. Sci. USA, 87,* 7380-7384 (1990).

Kohno et al., "A Second Tumor Necrosis Factor Receptor Gene Product Can Shed a Naturally Occuring Tumor Necrosis Factor Inhibitor ", *Proc. Natl. Acad. Sci. USA, 87,* 8331-8335 (1990).

Arakawa et al., "Protein-Solvent Interactions in Pharmaceutical Formulations", *Pharmaceutical Research, 8,* No. 3, 285-291 (1991).

Serge N. Timasheff, "The Control of Protein Stability and Association by Weak Interactions with Water: How Do Solvents Affect These Processes?" *Annu. Rev. Biophys. Biomol. Struct., 22,* 67-97 (1993).

Kita et al., "Contribution of the Surface Free Energy Perturbation to Protein-Solvent Interactions ", *Biochemistry, 33,* 15178-15189(1994).

Serge N. Timasheff, "Solvent Stabilization of Protein Structure ", *Methods in Molecular Biology, 40,* 253-269 (1995).

Johnson et al., "A Month-Long Effect From a Single Injection of Microencapsulated Human Growth Hormone ", *Nature Medicine, 2,* No. 7, 795-799 (1996).

Lin et al., "On the Role of Surface Tension in the Stabilization of Globular Proteins ", *Protein Science, 5,* 372-381 (1996).

Smith et al., "A Novel Parenteral Delivery System ", *Pharmaceutical Research, 13,* No. 3, 300 (1996).

Xie et al., "The Thermodynamic Mechanism of Protein Stabilization by Trehalose ", *Biophysical Chemistry, 64,* 25-43 (1997).

Maa et al., "Spray-Drying of Air-Liquid Interface Sensitive Recombinant Human Growth Hormone", *Journal of Pharmaceutical Sciences, 87* No. 2, 152-159 (1998).

Serge N. Timasheff, "Control of Protein Stability and Reactions by Weakly Interacting Cosolvents: The Simplicity of the Complicated", *Advances in Protein Chemistry, 51,* 355-432 (1998).

Sackett et al., "Multivalent Cations Depress Ligand Binding to Cell-Associated Insulin-Like Growth Factor Binding Protein-5 on Human Glioblastoma Cells", *Endocrinology, 139,* No. 4, 1943-1951 (1998).

Lai et al., "Metal and RNA Binding Properties of the hdm2 Ring Finger Domain ", *Biochemistry, 37,* No. 48, 17005-17015 (1998).

Yang et al., "Effect of Zinc Binding and Precipitation on Structures of Recombinant Human Growth Hormone and Nerve Growth Factor ", *Journal of Pharmaceutical Sciences, 89,* No. 11, 1480-1485 (2000).

Bartus, et al., "Sustained delivery of proteins for novel therapeutic agents", (1998) Science, vol. 281, pp. 1161-1162.

* cited by examiner

SUSTAINED RELEASE FORMULATIONS

This application claims the benefit of Provisional Application Ser. No. 60/198,209, filed Apr. 19, 2000, the disclosure of witch is hereby incorporated by reference.

BACKGROUND OF THE INVENTION

1. Field of the Invention

This invention relates to sustained release preparation of growth hormone, especially human growth hormone.

2. Description of Related Disclosures

Sustained release delivery systems are of interest because they can improve patient compliance, tolerability, product performance, and expand the market potential for a product. The SABER system is a novel injectable liquid non-polymeric drug delivery system (Smith and Tipton (1996) Pharmaceutical Research 13(3):300). The SABER system, which stands for Sucrose Acetate isoButyrate Extended Release, is composed of sucrose acetate isobutyrate (SAIB) and a plasticizing solvent. SABER is injected as a low viscosity liquid that increases rapidly in viscosity after injection. The resulting high viscosity matrix is adhesive, biodegradable and biocompatible.

Clinically, rhGH is administered daily in growth hormone deficient (GHD) patients. To decrease the dosing frequency and increase patient compliance several sustained release formulations are under development. Recently the FDA approved the first rhGH sustained release formulation. This formulation allows patients to decrease their dosing interval from daily to once or twice per month depending on rhGH requirements. However, the approved Depot formulation releases 10–20% of the encapsulated protein in the first two days leading to high rhGH serum levels (Johnson et al., (1996) Nature Medicine (2):795–799).

SUMMARY OF THE INVENTION

The present invention provides novel non-polymeric sustained release formulations of growth hormone.

BRIEF DESCRIPTION OF THE DRAWINGS

FIG. 2: The effect of solvent ratio (FIG. 2A) and loading (FIGS. 2B and 2C) on the release of hGH from sucrose acetate isobutyrate formulations containing ethanol.

DETAILED DESCRIPTION OF THE PREFERRED EMBODIMENTS

Modes for Carrying Out the Invention

The purpose of this study was to evaluate the release of recombinant human growth hormone (rhGH) from a non-polymeric sucrose acetate isobutyrate sustained release system.

The system comprised sucrose acetate isobutyrate (SAIB) and a solvent. Two spray freeze dried formulations of rhGH were evaluated, rhGH in sodium bicarbonate and rhGH complexed with zinc. The rhGH powders were homogenized with various systems at two different protein loads (5 and 15% w/v). The release rate and protein stability was monitored by reverse phase-HPLC, size exclusion chromatography and BCA for 28 days. The effect of zinc and surface area on release rate and protein stability was also investigated.

The in vitro results for the zinc complexed rhGH indicated a very low burst from 0.1 (SAIB:Ethanol) to 2.2% (SAIB:Miglyol) followed by protein release over 28 days. The release rates and total protein released by the different preparations varied widely. The high protein load (15%) and the low protein load (5%) released approximately the same amount of protein indicating that the surface area of the sucrose acetate isobutyrate:solvent/protein mix proved to be an important factor in the initial burst and the release rate. In vitro experiments that increased the surface area of the sucrose acetate isobutyrate:solvent/protein in contact with the release medium resulted in increased bursts of 1 to 4% with a higher total percentage of released protein. The bicarbonate rhGH suspension had a higher initial burst (7 to 14%) and released more protein in 28 days when compared to the zinc complexed rhGH suspension.

Changing the solvent polarity, the ratio of solvent to SAIB, and the addition of zinc can modify the release rate of the rhGH from sucrose acetate isobutyrate:solvent systems. These results demonstrate that the sucrose acetate isobutyrate:solvent delivery system is capable of providing sustained release of intact rhGH in vitro.

Sucrose acetate isobutyrate extended release systems are described in U.S. Pat. No. 5,747,058, for example, the disclosure of which is specifically incorporated herein by reference.

The growth hormone (GH) is preferably human growth hormone (hGH), preferably biologically active non-aggregated hGH. According to the present invention the GH is complexed with at least one type of multivalent metal cation, preferably having a valence of +2 or more, preferably from a metal cation component of the formulation.

Suitable multivalent metal cations include biocompatible and non-toxic metal cations. A preferred metal cation component for GH is $Zn^{+2}$. Typically, the molar ratio of metal cation component to GH is between 1:1 and 100:1, preferably, between 1:1 and 20:1 and preferably between 1:1 and 10:1.

The following examples are offered by way of illustration and not by way of limitation. The disclosures of all citations in the specification are expressly incorporated herein by reference.

EXAMPLES

Example I

Methods

Preparation of zinc complexed rhGH: A 20 mg/ml rhGH solution in 25 mM sodium bicarbonate was complexed with zinc at a rhGH:zinc ratio of 10:1. The rhGH/zinc suspension was spray freeze dried to create a fine powder that is approximately 70% rhGH by weight.

Preparation of bicarbonate rhGH: A solution of approximately 5 mg/ml rhGH in 10 mM ammonium bicarbonate was lyophilized to produce an excipient free powder.

SAIB/rhGH suspension preparation: The rhGH SABER suspensions were prepared by mixing rhGH powders with SABER formulations using a shear homogenizer. Release Rate Determination: 0.2 mL of each rhGH/SAIB suspension was added to eppendorf tubes in duplicate, then 0.5 mL of release medium (50 mM HEPES, 10 mM KCl, 0.1% NaN3, pH 7.2) was added above the suspension. The eppendorf tubes were incubated at 37 deg. C. and sampled at various time points. At each time point, 0.5 mL of release medium was removed and 0.5 mL of fresh release medium added. Collected samples were stored at −70 deg. C. prior to analysis. The release samples were analyzed for protein concentration and protein quality.

BCA Assay: The BCA assay in a microtiter plate format was used to determine the protein concentration of the release samples. rhGH protein standards were prepared in release medium at 0, 0.005, 0.01, 0.02, 0.05, 0.2, 0.5 g/ml. 0.02 mL of each blank, standards, and release samples were mixed with 0.2 mL of the BCA working reagent in a microtiter plate. The microtiter plate was incubated at 37 deg. C. for 1 hr and the absorbance determined at 562 nm using a microtiter plate reader. The protein concentrations of the release samples were determined from the standard curve using a four parameter non-linear curve fit. The amount of oxidized variants in the rhGH release samples was determined by RP-HPLC. This assay was run using a 4.6×15 cm, 8 mm, 300 angstrom PLRPS column held at room temperature. The mobile phase A contained 50 mM NaH2PO4, pH 7.0 and mobile phase B contained 20% propanol in acetonitrile. The separation was isocratic at 49% (B) and the eluent was monitored for absorbance at 214 nm.

Size Exclusion Chromatography was used to determine amount of monomer present in the release samples. This assay was run using a 7.8×300 mm TSK 2000SWXL column held at room temperature. The mobile phase used was 50 mM NaH2PO4, 150 mM NaCl pH 7.2 with a flow rate of 1.0 ml/min and a run time of 20 min. 10 g protein was injected and the eluent monitored for absorbance at 214 nm.

In vivo pharmacokinetics of rhGH were determined in after SC injection of rhGH SABER formulations (SAIB: Benzyl alcohol; 85:15 w/w and SAIB:Benzyl benzoate; 70:30 w/w) in Sprague Dawley (SD) rats. Serum rhGH levels were determined by ELISA (Genentech) with an assay detection limit of 0.1 ng/mL.

Results and Discussion

Solvent Ratio

Figure 1:
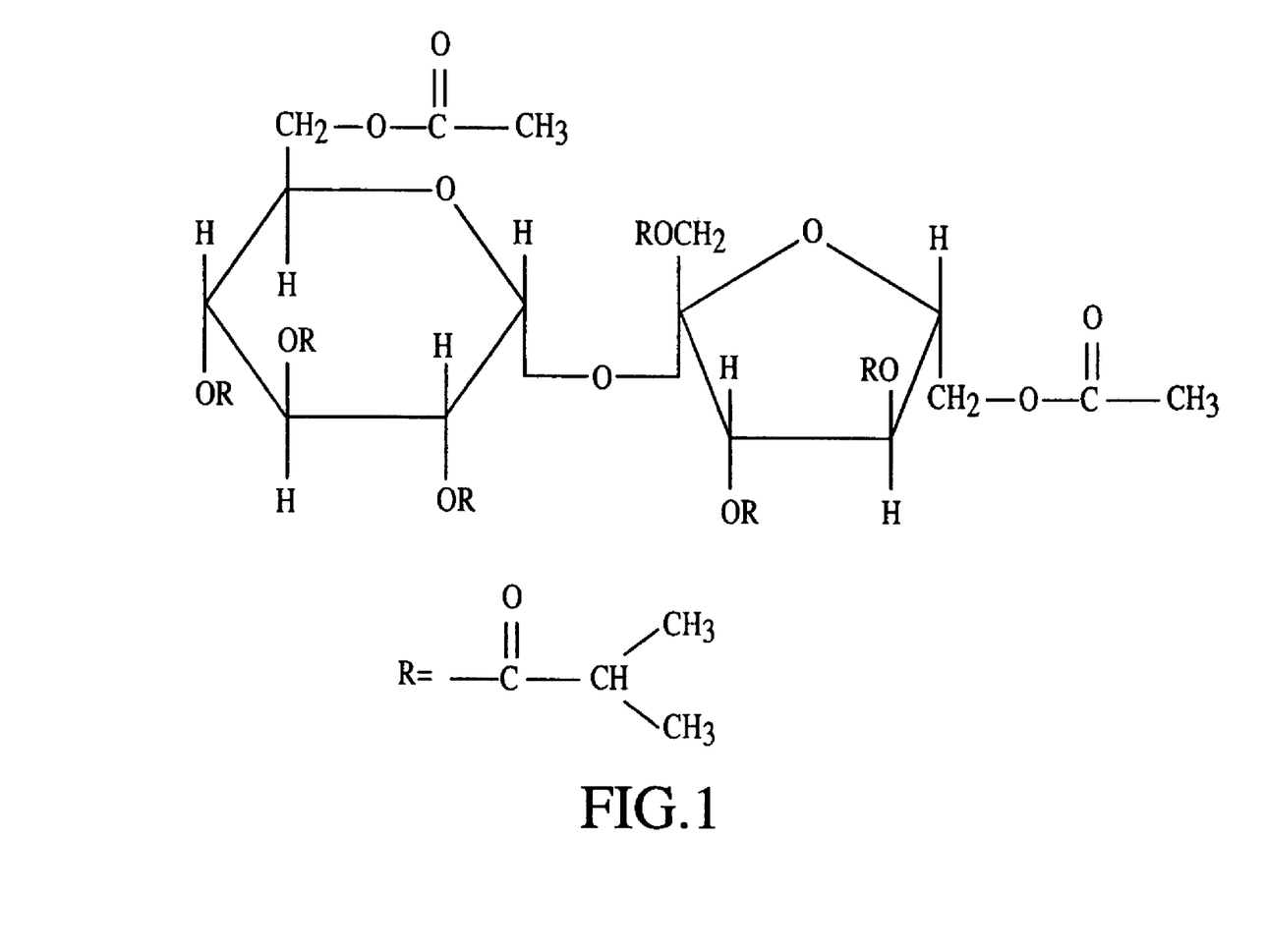
FIG. 1: The structure of sucrose acetate isobutyrate is shown in FIG. 1.
Figure 2:
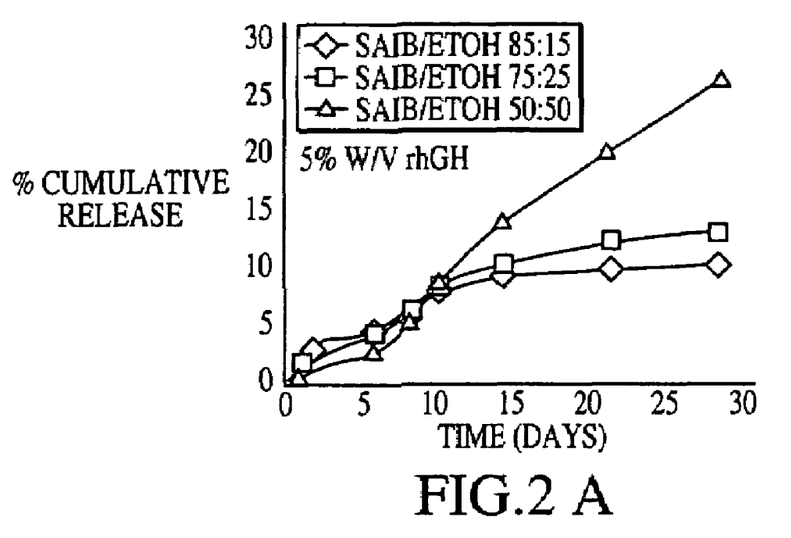

The effect of the SAIB/solvent ratio on protein released was examined by plotting the cumulative release for rhGH in SAIB:ethanol ratios, 85:15, 75:25, and 50:50 (w/w). This plot is shown in FIG. 2A. The 85:15, 75:25, and 50:50 w/w ratio resulted in a 10%, 13%, and 26% release of the protein at 28 days. The SAIB/solvent ratio is a factor in release rate, but it does not effect the initial burst for the SAIB:ethanol formulations.

SABER Solvent Type

Figure 3:
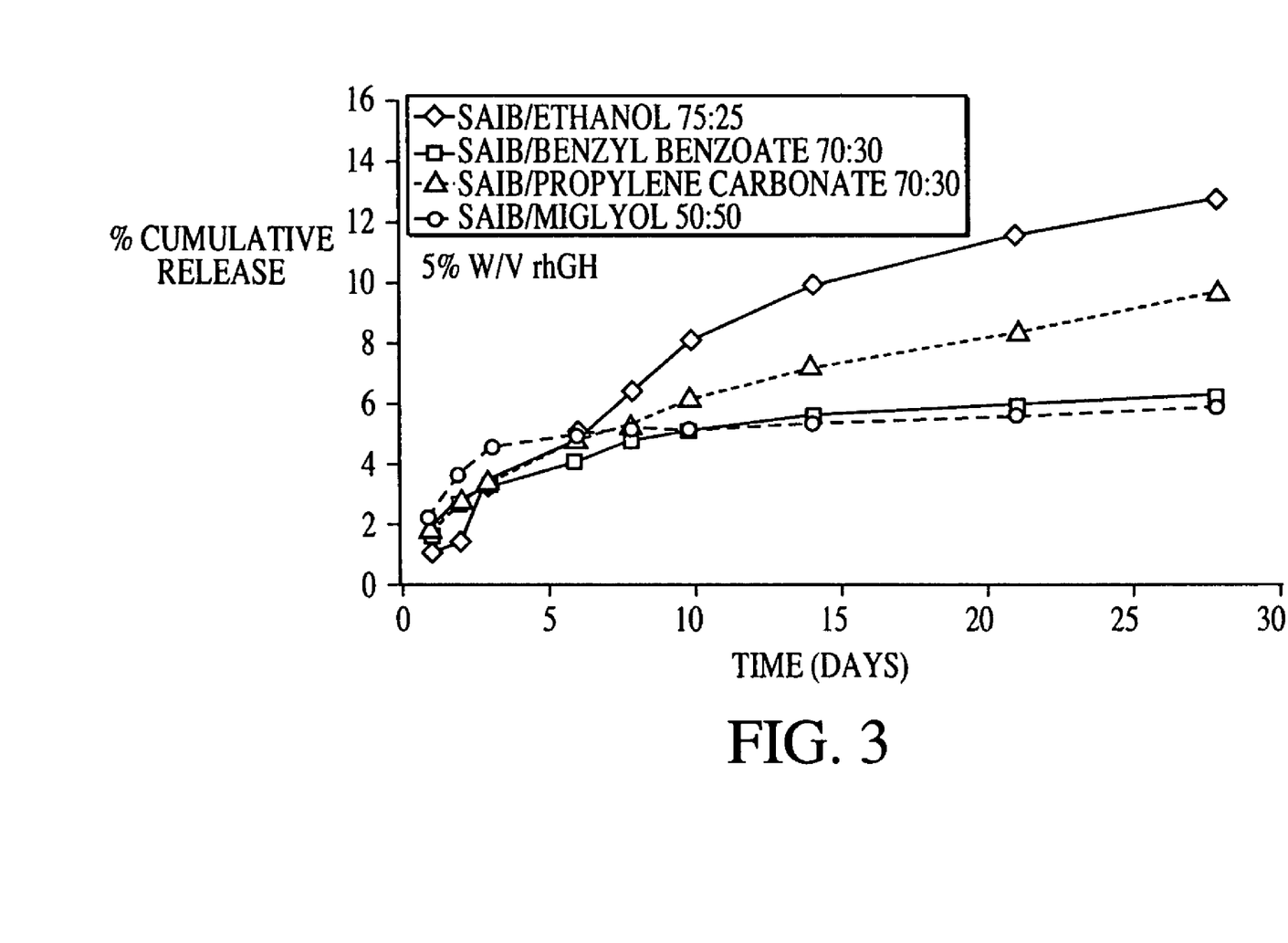
FIG. 3: The effect of solvent on the release of rhGH from sucrose acetate isobutyrate formulations.

The effect of solvent on the rate of release from SABER is shown in FIG. 3. All SAIB/solvent preparations show a low initial burst of rhGH in the first day and protein release out to 28 days. The rhGH/SAIB:miglyol suspension was the only sample with a poor release curve. The total amount of protein released over the 28 days for all samples was no higher than 13% of the total protein load. This result was expected due to the lack of enzymatic degradation in these in vitro experiments.

Loading

Figure 2B:
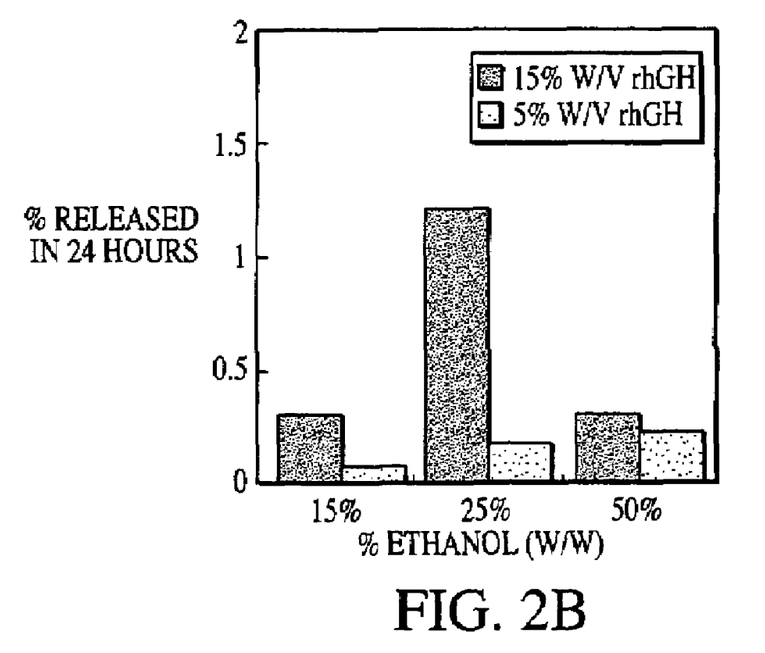
Figure 2C:
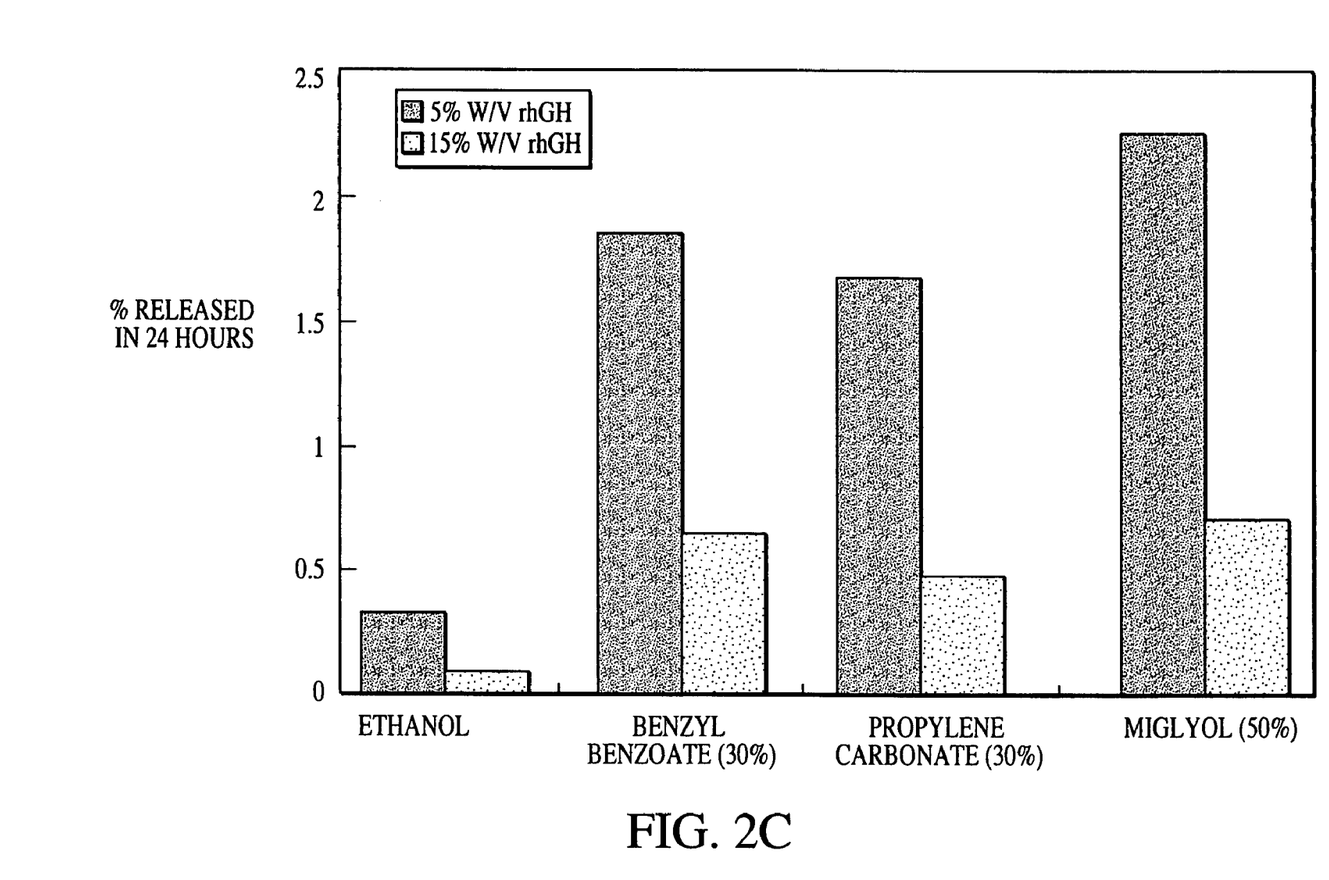

The release results for all SAIB/solvent preparations and both protein loads are detailed in FIGS. 2B–C. Ideally a one month sustained release system should have an initial burst of approximately <10% and an average daily release of 3%. The results for the SABER with rhGH show a burst from 0.1 to 2.2%, with an average daily release over 28 days from 0.1 to 0.9%. These values are extremely low but expected due to the lack of in vitro degradation of SABER.

Formulation

Figure 4:
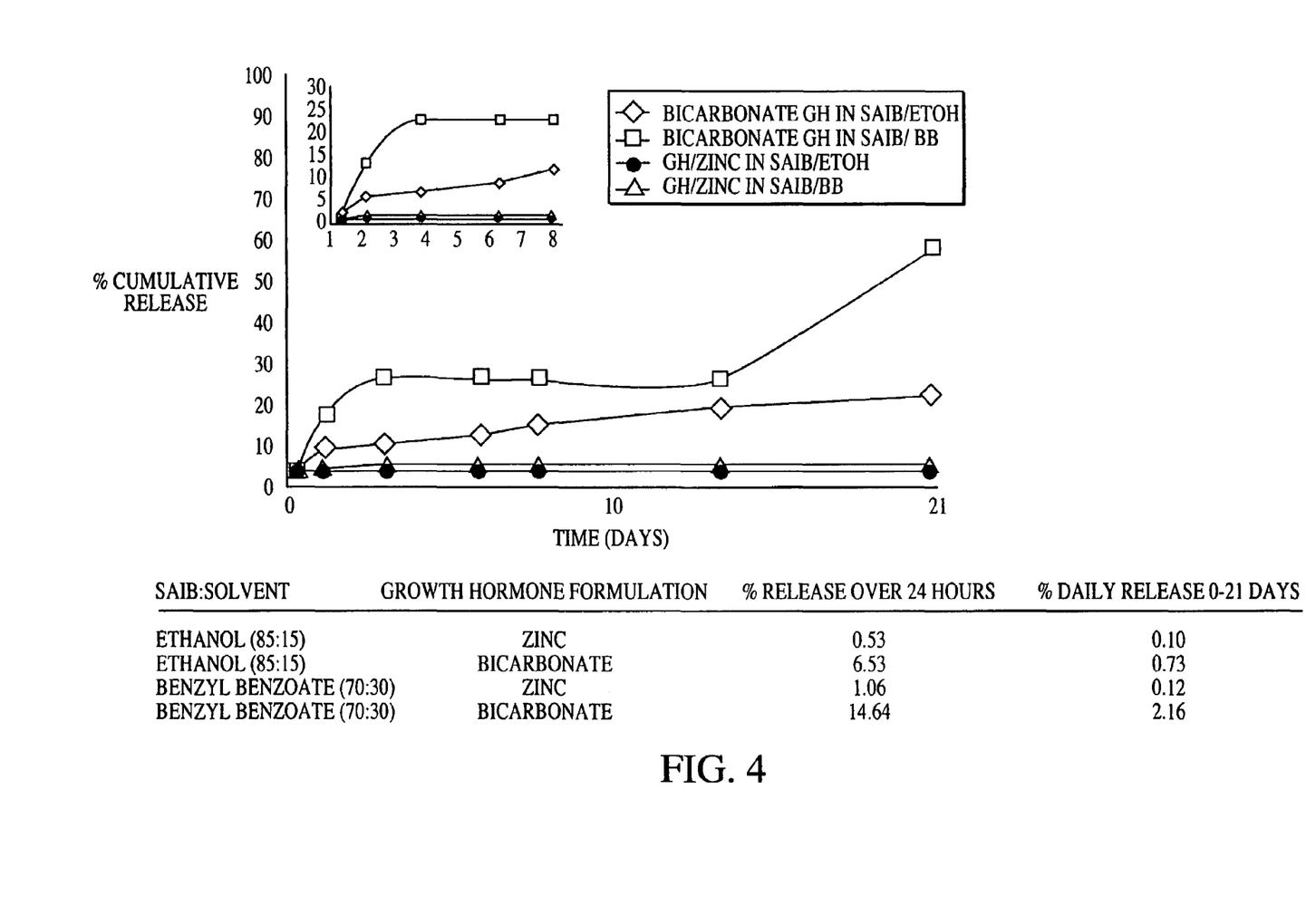
FIG. 4: The effect protein formulation has on the relapse of rhGH from sucrose acetate isobutyrate formulations.
Figure 5:
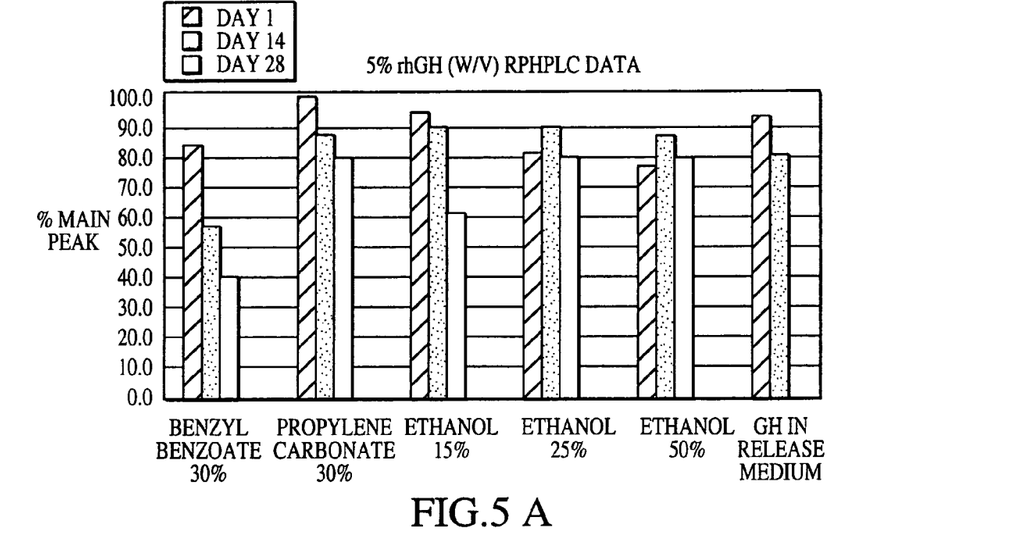
FIG. 5: Protein integrity after relapse from sucrose acetate isobutyrate formulations determined by native size exclusion chromatography and reverse phase HPLC.
Figure 6:
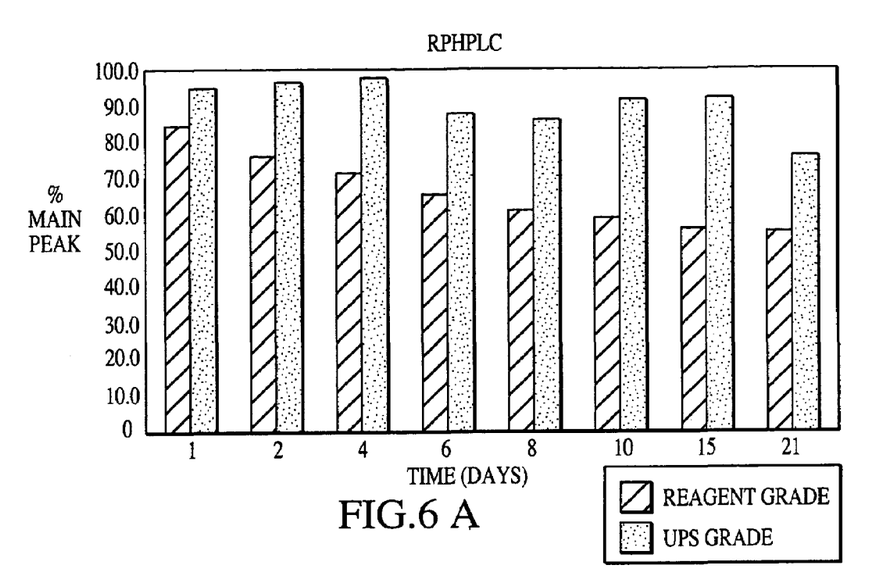
FIG. 6: Effect of solvent quality on stability of rhGH released from sucrose acetate isobutyrate formulations containing reagent and USP grade benzyl benzoate.

The effect of zinc on rhGH release from SABER was evaluated by comparing release rates of zinc complexed rhGH and lyophilized rhGH in bicarbonate from SABER. 5% w/v suspensions were prepared using two SAIB/solvent preparations, benzyl benzoate, and ethanol. The release curves are shown in FIG. 4. The bicarbonate rhGH produces a higher initial burst than the zinc complexed rhGH for both SABER preparations. The initial burst for the bicarbonate rhGH from SAIB:ethanol is 6.53% compared to 0.53% for the zinc complexed rhGH. The initial burst from SAIB: benzyl benzoate is 14.64% for the bicarbonate rhGH compared to 1.06% for the zinc complexed rhGH. The daily release and the overall total protein released is also much higher for the bicarbonate rhGH. These results indicate that excipients such as zinc can affect protein release from SABER. This effect may be due to differences in particle morphology or more likely differences in protein solubility. Zinc complexed rhGH has lower solubility than the bicarbonate formulation. The integrity of the released protein was determined by RP-HPLC and SEC. The results indicate a decrease in native protein over time (FIG. 5). This decrease was most pronounced in protein released from SABER formulations containing benzyl benzoate and ethanol. Protein released from the 5% load formulations was less native than protein released from the 15% load formulations. This may be due to a decrease in the protein:solvent ratio in the 5% load formulations, leading to higher solvent exposure in the release medium. During the course of these experiments several grades of benzyl benzoate were used (reagent grade and USP grade). Samples from experiments using these solvent grades were tested for oxidation (RP-HPLC) and aggregation (SEC). The results show protein released from the SABER formulations containing USP grade benzyl benzoate were less degraded than protein released from reagent grade benzyl benzoate (FIG. 6) After 21 days the amount of rhGH monomer remaining was over 90% for the USP grade benzyl benzoate formulation compared to 75% for the reagent grade formulation. The reversed phase results also show an improvement in protein quality with the USP grade benzyl benzoate. At 21 days 80% of the main peak remained compared to 60% seen with the reagent grade solvent. The purity of solvent used in SABER formulations has a direct effect on protein quality and thus should be monitored.

Figure 7:
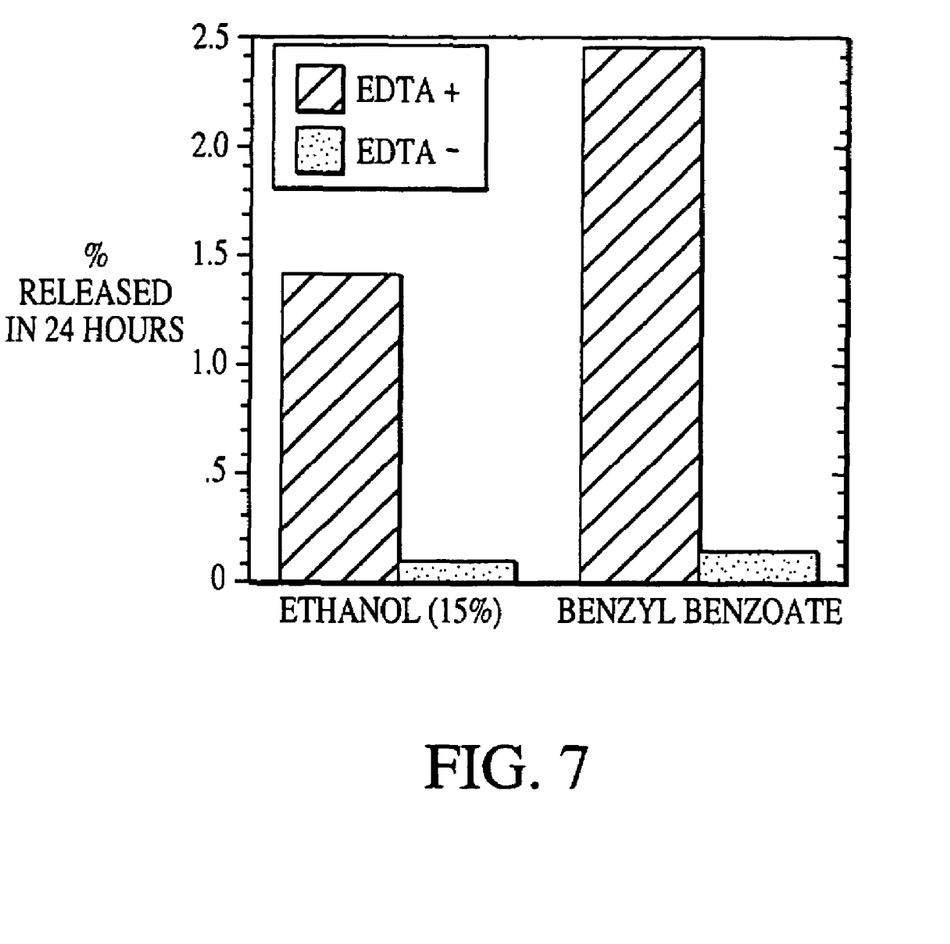
FIG. 7: The effect a chelating agent (EDTA) has on the relapse of zinc complexed rhGH from sucrose acetate isobutyrate formulations.

To determine the effect zinc had on the protein release rate, zinc complexed GH and bicarbonate rhGH were mixed with two SABER formulations containing ethanol and benzyl benzoate as solvents. In vitro release experiments were carried out using an EDTA containing release medium (50 mM HEPES, 10 mM KCl, 50 mM EDTA, 0.1% NaN3, pH 7.2). These results are summarized in FIG. 7. The presence of EDTA in the release medium increased both the initial burst and the overall release for both rhGH SABER formulations.

Surface Area

Figure 8:
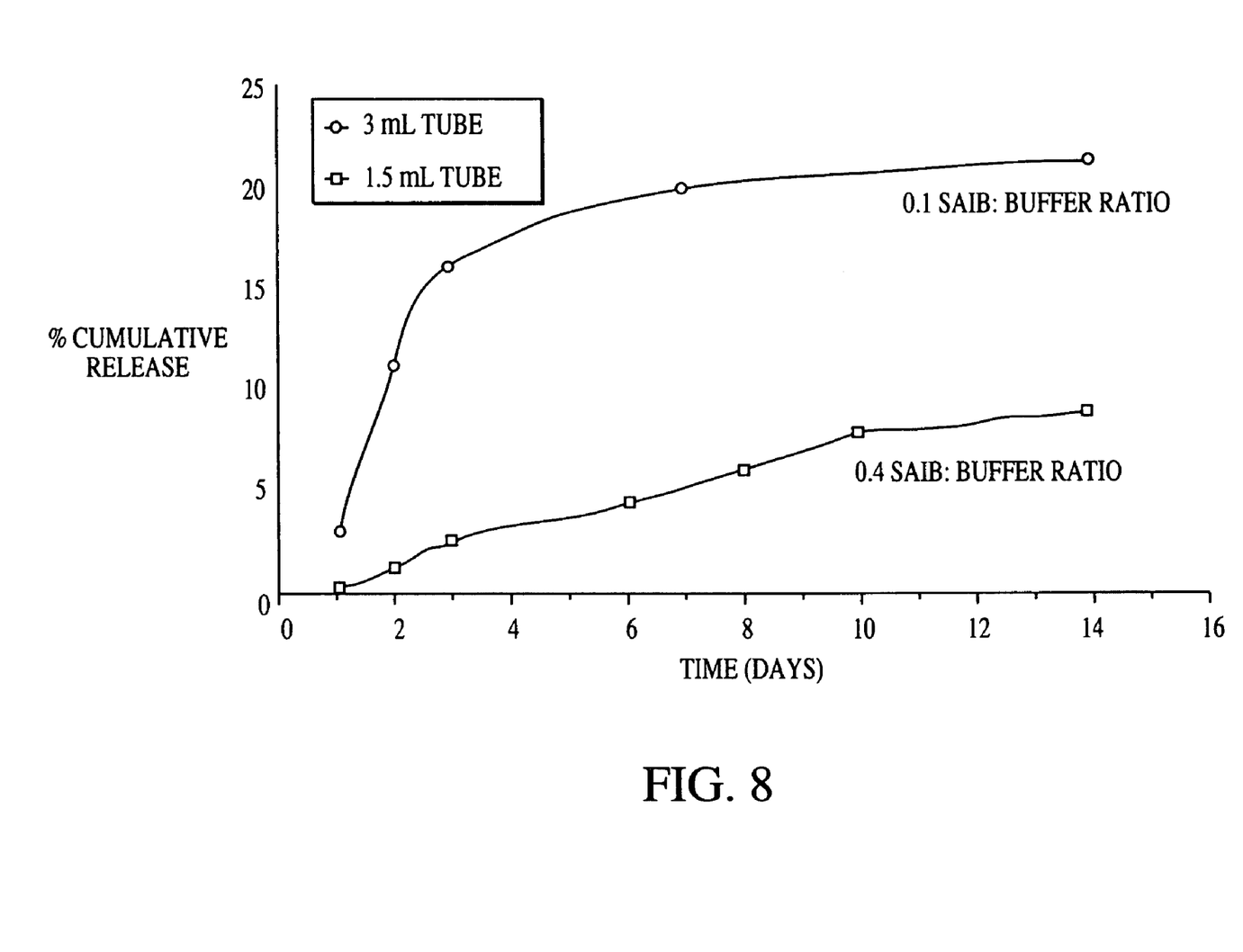
FIG. 8: The effect buffer exposed surface area and sucrose acetate isobutyrate buffer ratio have on the relapse of rhGH from sucrose acetate isobutyrate formulations.

Exposed solvent accessible surface area and SABER: buffer ratio appeared to influence release of rhGH from SABER formulations (FIG. 8). When a larger surface area and lower SABER:buffer ratio (>buffer volume) was used more rhGH was released. This result indicates that both exposed surface area and SABER:buffer ratio should be controlled during in vitro experiments.

Pharmacokinetics

Figure 9:
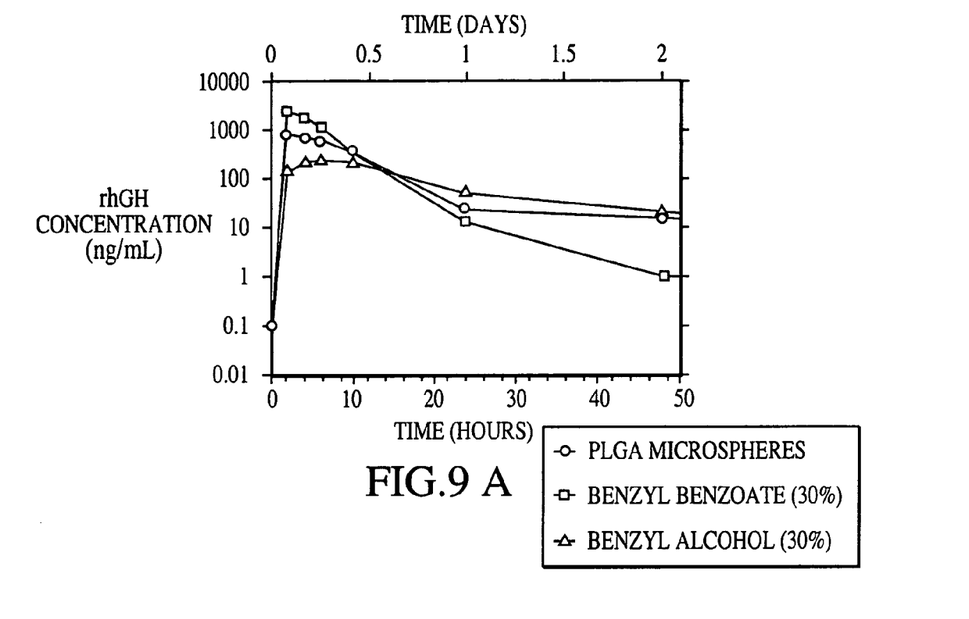
FIG. 9: rhGH serum levels after subcutaneous administration of rhGH sucrose acetate formulation (SD rats 6/group, 15 mg/Kg).

In vivo pharmacokinetics show SABER formulations are able to deliver rhGH for prolonged periods of time with a fairly low initial burst (FIG. 9). However, SABER solvent properties play a large role in the release mechanism. The SABER formulation containing benzyl benzoate released >80% of available loaded material in the first 48 hrs while the benzyl alcohol formulation delivered target (10 ng/mL) levels of rhGH for the duration of these studies. When compared to control microspheres the benzyl alcohol formulation had a significantly lower initial burst yet maintained similar serum levels for 7 days.

Conclusions

In vitro release kinetics are dependent on SAIB/Solvent type, SAIB/Solvent ratio, excipients, release medium, and surface area.

The quality of the released protein is dependent upon the type of solvent and purity of solvent used in the SABER preparation. The rhGH SABER formulations can provide a low burst, sustained release system for delivery of rhGH. However in vivo kinetics could depend on protein formulation and SABER solvent choice.

What is claimed is:

1. A composition for sustained release, comprising:
   a carrier material comprising a non-polymeric, non-water soluble liquid material having a viscosity of at least 5,000 cP at 37° C. that does not crystallize neat under ambient physiological conditions;
   growth hormone; and
   a multivalent metal cation;
   wherein the composition releases at most 4% of the growth hormone in vitro within the first 24 hours as determined by Release Rate Determination.

2. The composition of claim 1, wherein the liquid material is a stearate ester, a stearate amide, a long-chain fatty acid amide, a long-chain fatty alcohol, a long-chain ester, or a disaccharide ester.

3. The composition of claim 1, wherein the liquid material is acetylated sucrose distearate.

4. The composition of claim 1, wherein the liquid material is disaccharide acetate butyrate.

5. The composition of claim 4, wherein the liquid material is sucrose acetate isobutyrate.

6. The composition of claim 5, wherein the growth hormone is human growth hormone.

7. The composition of claim 5, wherein the multivalent metal cation has a valence of two.

8. The composition of claim 7, wherein the multivalent metal cation is $Zn^{2+}$.

9. The composition of claim 5, further comprising a solvent.

10. A composition for sustained release, comprising:
    sucrose acetate isobutyrate;
    a solvent;
    zinc; and
    growth hormone;
    wherein the composition releases at most 4% of the growth hormone in vitro within the first 24 hours as determined by Release Rate Determination.

11. The composition of claim 10, wherein the composition has a viscosity less than 1000 cP at room temperature.

12. The composition of claim 10, wherein the composition has a viscosity less than 200 cP at room temperature.

13. The composition of claim 10, wherein the solvent is ethanol, benzyl benzoate, miglyol, propylene carbonate, benzyl alcohol, ethyl lactate, glycofurol, N-methylpyrrolidone, 2-pyrrolidone, propylene glycol, acetone, methyl acetate, ethyl acetate, methyl ethyl ketone, triacetin, dimethylformamide, dimethylsulfoxide, tetrahydrofuran, caprolactam, decylmethylsulfoxide, oleic acid, or 1-dodecyazacycloheptan-2-one.

14. The composition of claim 10, wherein the solvent is ethanol, benzyl benzoate, miglyol, propylene carbonate, or benzyl alcohol.

15. The composition of claim 10, wherein the ratio of sucrose acetate isobutyrate to solvent is from 50:50 w/w to 85:15 w/w.

16. The composition of claim 10, wherein the ratio of sucrose acetate isobutyrate to solvent is from 50:50 w/w to 75:25 w/w.

17. The composition of claim 10, wherein the ratio of sucrose acetate isobutyrate to solvent is from 50:50 w/w to 70:30 w/w.

18. The composition of claim 10, wherein the molar ratio of zinc to growth hormone is from 100:1 to 1:1.

19. The composition of claim 10, wherein the molar ratio of zinc to growth hormone is from 20:1 to 1:1.

20. The composition of claim 10, wherein the molar ratio of zinc to growth hormone is from 10:1 to 1:1.

21. The composition of claim 10, comprising:
    a sucrose acetate isobutyrate to solvent ratio from 50:50 w/w to 85:15 w/w, wherein the sucrose acetate isobutyrate and solvent together form a liquid; and
    a zinc to growth hormone molar ratio from 100:1 to 1:1, wherein the zinc and growth hormone together form a complex.

22. The composition of claim 21, wherein the ratio of sucrose acetate isobutyrate to solvent is from 50:50 w/w to 75:25 w/w.

23. The composition of claim 21, wherein the ratio of sucrose acetate isobutyrate to solvent is from 50:50 w/w to 70:30 w/w.

24. The composition of claim 21, wherein the molar ratio of zinc to growth hormone is from 20:1 to 1:1.

25. The composition of claim 21, wherein the molar ratio of zinc to growth hormone is from 10:1 to 1:1.

26. A method of administering growth hormone, comprising:
    injecting the composition of claim 1 into a patient in need of said growth hormone.

27. The method of claim 26, wherein less than 0.2% of the growth hormone is released within 24 hours of administration.

28. The method of claim 26, wherein the percentage of the growth hormone released within a 24 hour period is from 0.05% to 3%.

29. The method of claim 26, wherein the percentage of the growth hormone released within a 24 hour period is from 1% to 3%.

30. A method of administering growth hormone, comprising:
injecting the composition of claim 10 into a patient in need of said growth hormone.

31. The method of claim 30, wherein less than 0.2% of the growth hormone is released within 24 hours of administration.

32. The method of claim 30, wherein the percentage of the growth hormone released within a 24 hour period is from 0.05% to 3%.

33. The method of claim 30, wherein the percentage of the growth hormone released within a 24 hour period is from 1% to 3%.

34. A method of administering growth hormone, comprising:
injecting the composition of claim 21 into a patient in need of said growth hormone.

35. The method of claim 34, wherein less than 0.2% of the growth hormone is released within 24 hours of administration.

36. The method of claim 34, wherein the percentage of the growth hormone released within a 24 hour period is from 0.05% to 3%.

37. The method of claim 34, wherein the percentage of the growth hormone released within a 24 hour period is from 1% to 3%.

38. A method of making a sustained release composition, comprising:
mixing a complex and a liquid carrier to form said sustained release composition;
wherein said liquid carrier comprises sucrose acetate isobutyrate; and
wherein said complex comprises growth hormone and $Zn^{2+}$;
wherein said sustained release composition releases at most 4% of the growth hormone in vitro within the first 24 hours as determined by Release Rate Determination.

39. The method of claim 38, wherein said sustained release composition has a viscosity less than 1000 cP at room temperature.

40. The method of claim 38, wherein said sustained release composition has a viscosity less than 200 cP at room temperature.

41. The method of claim 38, wherein the molar ratio of zinc to growth hormone is from 100:1 to 1:1.

42. The method of claim 38, wherein the molar ratio of zinc to growth hormone is from 10:1 to 1:1.

43. The method of claim 38, wherein said liquid carrier further comprises a solvent.

44. The method of claim 43, wherein said solvent is ethanol, benzyl benzoate, miglyol, propylene carbonate, or benzyl alcohol.

45. The method of claim 43, wherein the ratio of sucrose acetate isobutyrate to solvent is from 50:50 w/w to 85:15 w/w.

46. The method of claim 43, wherein the ratio of sucrose acetate isobutyrate to solvent is from 50:50 w/w to 70:30 w/w.

47. The method of claim 43, wherein said sustained release composition comprises:
a sucrose acetate isobutyrate to solvent ratio from 50:50 w/w to 85:15 w/w, wherein the sucrose acetate isobutyrate and solvent together form said liquid carrier;
a zinc to growth hormone molar ratio from 100:1 to 1:1, wherein the zinc and growth hormone together form said complex; and
a liquid carrier to complex ratio from 95:5 v/w to 85:15 v/w.

48. The method of claim 47, wherein the ratio of sucrose acetate isobutyrate to solvent is from 50:50 w/w to 70:30 w/w.

49. The method of claim 47, wherein the molar ratio of zinc to growth hormone is from 10:1 to 1:1.

* * * * *